United States Patent
Szczerbinska et al.

(10) Patent No.: US 12,104,168 B2
(45) Date of Patent: Oct. 1, 2024

(54) CELL CULTURE MEDIUM

(71) Applicant: Agency For Science, Technology And Research, Singapore (SG)

(72) Inventors: Iwona Szczerbinska, Singapore (SG); Yun Shen Chan, Singapore (SG); Huck Hui Ng, Singapore (SG)

(73) Assignee: **AGENCY FOR SCIENCE, TECHNOLOGY AND RESEARCH (A*STAR)**, Singapore (SG)

( * ) Notice: Subject to any disclaimer, the term of this patent is extended or adjusted under 35 U.S.C. 154(b) by 807 days.

(21) Appl. No.: 17/054,108

(22) PCT Filed: May 10, 2019

(86) PCT No.: PCT/SG2019/050265
§ 371 (c)(1),
(2) Date: Nov. 9, 2020

(87) PCT Pub. No.: WO2019/216831
PCT Pub. Date: Nov. 14, 2019

(65) Prior Publication Data
US 2021/0371810 A1  Dec. 2, 2021

(30) Foreign Application Priority Data
May 10, 2018 (SG) .............. 10201803944U

(51) Int. Cl.
*C12N 5/00* (2006.01)
*C12N 5/071* (2010.01)

(52) U.S. Cl.
CPC ......... *C12N 5/0018* (2013.01); *C12N 5/0672* (2013.01); *C12N 5/0678* (2013.01); *C12N 5/068* (2013.01); *C12N 2501/01* (2013.01); *C12N 2501/105* (2013.01); *C12N 2501/11* (2013.01); *C12N 2501/12* (2013.01); *C12N 2501/13* (2013.01); *C12N 2501/135* (2013.01); *C12N 2501/16* (2013.01); *C12N 2501/165* (2013.01); *C12N 2501/727* (2013.01)

(58) Field of Classification Search
None
See application file for complete search history.

(56) References Cited

U.S. PATENT DOCUMENTS

2018/0055887 A1* 3/2018 Lu .................. C12N 5/0667

FOREIGN PATENT DOCUMENTS

| EP | 2412800 A1 | 2/2012 |
|---|---|---|
| WO | 2014/152321 A1 | 9/2014 |
| WO | 2015196072 A2 | 12/2015 |
| WO | 2016016894 A1 | 2/2016 |
| WO | 2016/200340 A1 | 12/2016 |

OTHER PUBLICATIONS

Reddiconto et al, Blood, 2012, 119(10): 2335-2345. (Year: 2012).*
Reddiconto G. et al., Targeting of GSK313 promotes imatinib-mediated apoptosis in quiescent CD34+ chronic myeloid leukemia progenitors, preserving normal stem cells. Blood, Jan. 18, 2012, vol. 119, No. 10, pp. 2335-2345 [Retrieved on Jul. 2, 2019] <DOI: 10.1182/BLOOD-2011-06-361261>p. 2336, Left column, Methods—Inhibitors, Cell cultures, p. 2339-2340, Combined treatment with IM and SB216763 enforces CML CD34+ stem/progenitor cell cycling, differentiation and apoptosis, Figures 20, 4A-C, 7A-B, Table 2.
International Search Report issued Jul. 29, 2019 for PCT/SG2019/050265 [Agency for Science, Technology and Research].

* cited by examiner

*Primary Examiner* — Allison M Fox
*Assistant Examiner* — Qinhua Gu
(74) *Attorney, Agent, or Firm* — Honigman LLP; Fernando Alberdi; Jonathan P. O'Brien

(57) ABSTRACT

The present invention relates to a cell culture medium for preparing liver, gastric, pancreatic, colon or intestinal adult stem cell isolated from adult tissue, as well as for maintaining such stem cell in the undifferentiated state. The cell culture medium comprises a base medium; an ABL and SRC dual kinase inhibitor/an ABL kinase inhibitor and a SRC kinase inhibitor; a mitogenic factor; a WNT signalling pathway activator; a stimulator for NAD+ and NADP+ generation; and a cAMP/PKA pathway activator. In a particular embodiment, the ABL and SRC dual kinase inhibitor is Dasatinib; the mitogenic factor is EGF; the WNT signalling pathway activator is R-Spondin 1; the stimulator for NAD+ and NADP+ generation is nicotinamide; and the cAMP/PKA pathway activator is cholera endotoxin.

8 Claims, 19 Drawing Sheets

Adult stem cell media (ASCM) composition

Basal media
- Advance DMEM
- HEPEs
- L-Glutamine
- N-2 supplement
- B-27 supplement Key components added
- EGF
- R-spondin1
- Nicotinamide
- Cholera endotoxin
- Dasatinib

| Component | Regulated pathways |
|---|---|
| EGF | Activated EGFR and downstream signaling pathway |
| R-Spondin 1 | Amplifies Wnt signaling pathway activation |
| Nicotinamide | Generates NAD+ and NADP+ which are coenzymes in enzymatic oxidation-reduction reactions in cellular processes such as glycolysis, citric acid cycle and electron transport chain |
| Cholera endotoxin | Activates adenylate cyclase and induces cAMP/PKA pathway |
| Dasatinib | Dual inhibitor of Abl and SRC family kinases |

Figure 1

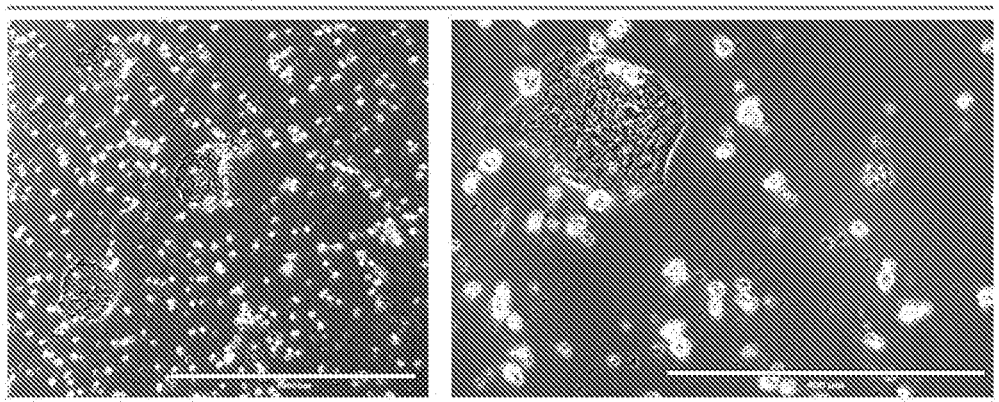
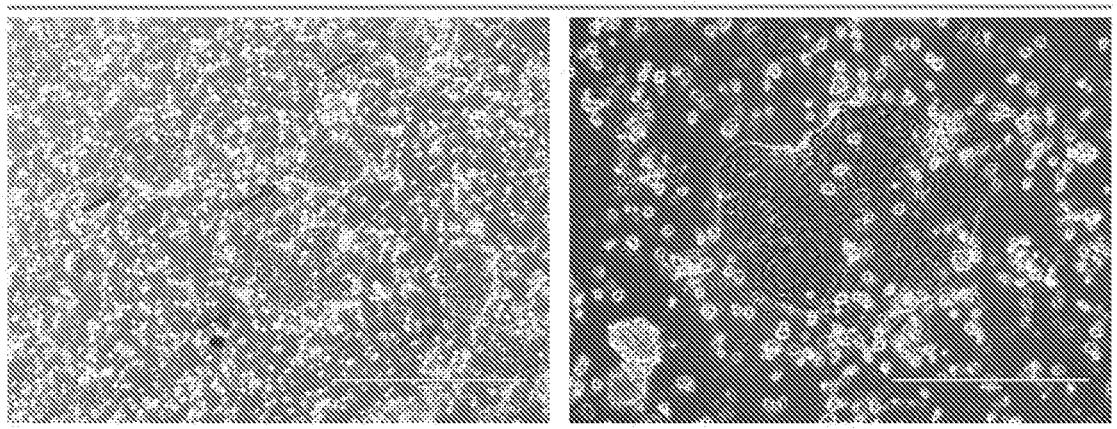
Figure 6

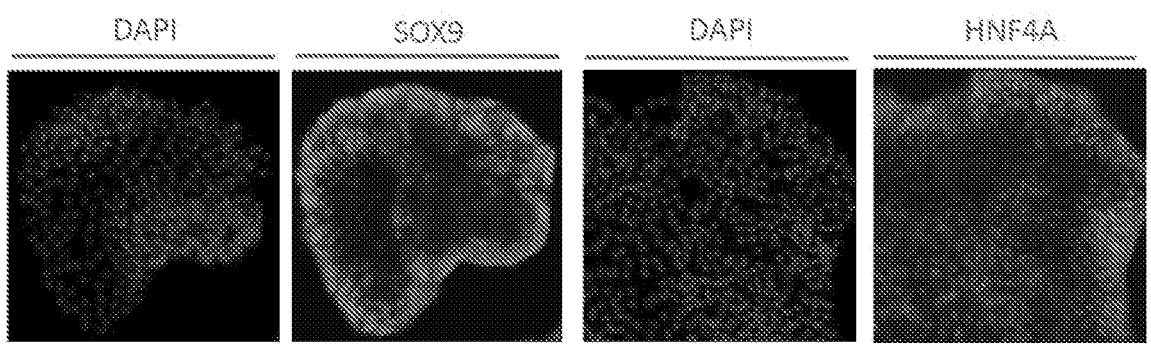
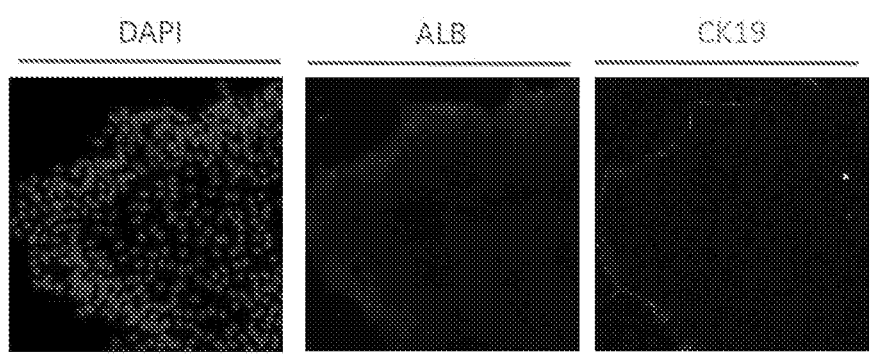
Figure 8

| Chemicals | Pathway targeted |
|---|---|
| Dasatinib | BCR-ABL tyrosine kinase inhibitor, also reported to inhibit SRC, c-KIT, PDGF and EPHA |
| Imatinib | BCR-ABL tyrosine kinase inhibitor, also reported to inhibit c-KIT and PDGF |
| Nilotinib | BCR-ABL tyrosine kinase inhibitor, also reported to inhibit c-KIT and PDGF |

Figure 10

Basal media
- Advance DMEM
- HEPEs
- L-Glutamine
- N-2 supplement
- B-27 supplement Key components added
- EGF
- R-spondin1
- Nicotinamide
- Cholera endotoxin
- Dasatinib

| Component | Regulated pathways |
|---|---|
| EGF | Activated EGFR and downstream signaling pathway |
| R-Spondin 1 | Amplifies Wnt signaling pathway activation |
| Nicotinamide | Generates NAD+ and NADP+ which are coenzymes in enzymatic oxidation-reduction reactions in cellular processes such as glycolysis, citric acid cycle and electron transport chain |
| Cholera endotoxin | Activates adenylate cyclase and induces cAMP/PKA pathway |
| Dasatinib | Dual inhibitor of Abl and SRC family kinases |

Figure 15

Basal media
- Advance DMEM
- HEPEs
- L-Glutamine
- N-2 supplement
- B-27 supplement Key components added
- EGF
- R-spondin1
- Nicotinamide
- Cholera endotoxin
- Dasatinib Optional molecules
- CHIR-98014

| Component | Regulated pathways |
|---|---|
| EGF | Activated EGFR and downstream signaling pathway |
| R-Spondin 1 | Amplifies Wnt signaling pathway activation |
| Nicotinamide | Generates NAD+ and NADP+ which are coenzymes in enzymatic oxidation-reduction reactions in cellular processes such as glycolysis, citric acid cycle and electron transport chain |
| Cholera endotoxin | Activates adenylate cyclase and induces cAMP/PKA pathway |
| Dasatinib | Dual inhibitor of ABL and SRC family kinases |

Figure 18

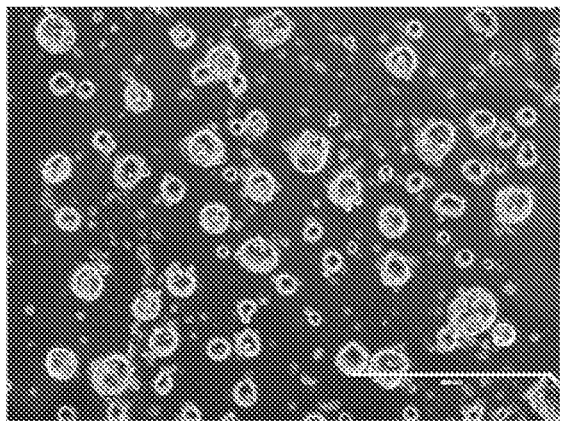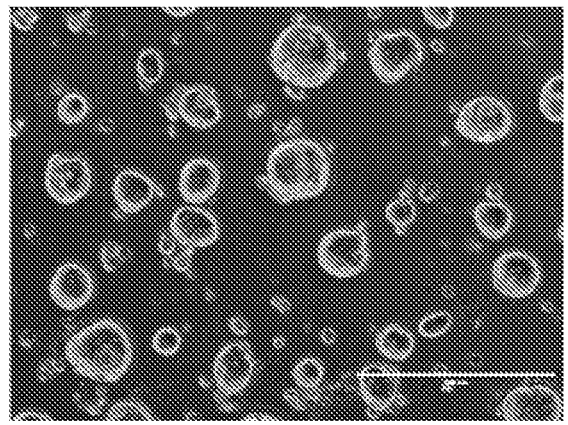
Figure 19

CELL CULTURE MEDIUM

CROSS-REFERENCE TO RELATED APPLICATIONS

This application is a 35 U.S.C. § 371 (c) United States National Phase application of, and claims priority to PCT Application No. PCT/SG2019/050265, filed May 10, 2019, which claims priority to Singapore Application Serial No. 10201803944U, filed on May 10, 2018. The entire contents of the aforementioned disclosures are incorporated by reference herein.

FIELD

The present invention relates to the field of cell culture. In particular, provided herein is a cell culture medium for preparing a stem cell from a differentiated cell or maintaining a stem cell in the undifferentiated state.

BACKGROUND

The endoderm is one of the three germ layers that is found in an embryo. The endoderm gives rise to a large array of highly specialised epithelial cell types that line the respiratory and digestive systems and contributes to organs such as thyroid, thymus, lungs, liver and pancreas. Organs that are derived from the endoderm provide many essential functions such as gas exchange, digestion, nutrient absorption, glucose homeostasis and detoxification.

The endoderm, mesoderm, and ectoderm, are formed during gastrulation. After gastrulation, the endoderm is transformed into a primitive gut tube surrounded by mesoderm, with a broad foregut, midgut and hindgut domains. The foregut gives rise to esophagus, trachea, stomach, lungs, thyroid, liver, biliary system, and pancreas. The midgut forms the small intestine, while the hindgut forms the large intestine.

The liver, for example, performs multiple critical functions to keep the body pure of toxins and harmful substances. In liver diseases, transplantation of the liver remains the gold standard of treatment to restore the function of the liver. The medical complexity of the procedure coupled with a severe lack of healthy liver graft availability creates an urgent need for more sustainable options. This unmet clinical need has spurred much effort to develop cellular transplantation as an alternative to whole organ transplantation. Besides clinical needs, liver cells (i.e. hepatocytes) are constantly used in the industry for in vitro toxicology screens.

In type 1 diabetes, an auto-immune mediated destruction of insulin producing beta cells in the pancreas reduces the body's ability to respond to glucose levels in the body. This results in hyperglycemia which has adverse short-term and long term consequences. There is therefore a great interest to develop pancreatic beta cells for use as a cellular therapy.

There is therefore a need to develop new cell culture protocols and media to obtain sufficient quantities of cells and stem cells for use in cellular therapies and in vitro studies.

SUMMARY OF THE INVENTION

The present invention discloses a cell culture medium and methods thereof for preparing a stem cell from a differentiated cell or maintaining a stem cell in the undifferentiated state.

In one aspect, there is provided a cell culture medium for preparing a stem cell from a differentiated cell or maintaining a stem cell in the undifferentiated state, the cell culture medium comprising:
 a) a base medium;
 b) an ABL and SRC dual kinase inhibitor, or an ABL kinase inhibitor and a SRC kinase inhibitor;
 c) a mitogenic factor; and
 d) a WNT signalling pathway activator.

In one embodiment, the differentiated cell is a differentiated cell from the Gut lineage.

In one aspect, there is provided a cell culture medium for preparing a stem cell from a differentiated cell or maintaining a stem cell in the undifferentiated state, the cell culture medium comprising:
 a) a base medium;
 b) an ABL kinase inhibitor and a SRC kinase inhibitor;
 c) a mitogenic factor; and
 d) a WNT signalling pathway activator.

In one aspect, there is provided a cell culture medium for preparing a stem cell from a differentiated cell or maintaining a stem cell in the undifferentiated state, the cell culture medium comprising:
 a) a base medium;
 b) an ABL and SRC dual kinase inhibitor;
 c) a mitogenic factor; and
 d) a WNT signalling pathway activator.

In one aspect, there is provided a method for preparing a stem cell from a differentiated cell, the method comprising contacting a differentiated cell with a cell culture medium as defined herein for a time and under conditions to derive a stem cell from the differentiated cell.

In one aspect there is provided a method for maintaining a stem cell in the undifferentiated state, the method comprising the step of culturing a stem cell with a cell culture medium as defined herein for a time and under conditions sufficient to maintain the stem cell in the undifferentiated state.

In one aspect, there is provided a stem cell obtained according to a method as defined herein.

BRIEF DESCRIPTION OF THE FIGURES

FIG. 1 shows the adult stem cell media (ASCM) composition used in the present invention.

FIG. 6 shows: A) Stem cells isolated from NOD-SCID mouse liver. Panel on left shows multiple stem cell colonies (arrow) growing from cells dissociated from liver tissue and plated on collagen coated dish. Panel on the right shows a typical liver stem cell colony. B) Liver stems cells isolated from mice of a different genetic background (C57BL/6). Panel on left shows multiple stem cell colonies (arrow) growing from cells dissociated from liver tissue and plated on collagen coated dish. Panel on the right shows a typical liver stem cell colony.

FIG. 8 shows the expression of stem cell markers in hepSC. HepSC expresses stem cell markers SOX9 and HNF4A (Panel top). HepSC do not express hepatocyte marker ALB or Cholangiocyte marker CK19 (Panel bottom).

FIG. 10 is a table showing the replacement of Dasatinib with other ABL kinase inhibitor.

FIG. 15 is a table showing that a similar strategy and protocol can be applied to adult pancreatic tissue to isolate pancreatic stem cells (PanSC).

FIG. 18 is a table showing that similar strategy and protocol can be applied to adult colon tissue to isolate colon stem cells (CoSC).

FIG. 19 shows the stable culture of the adult colon stem cells.

DETAILED DESCRIPTION OF THE INVENTION

Figure 2:
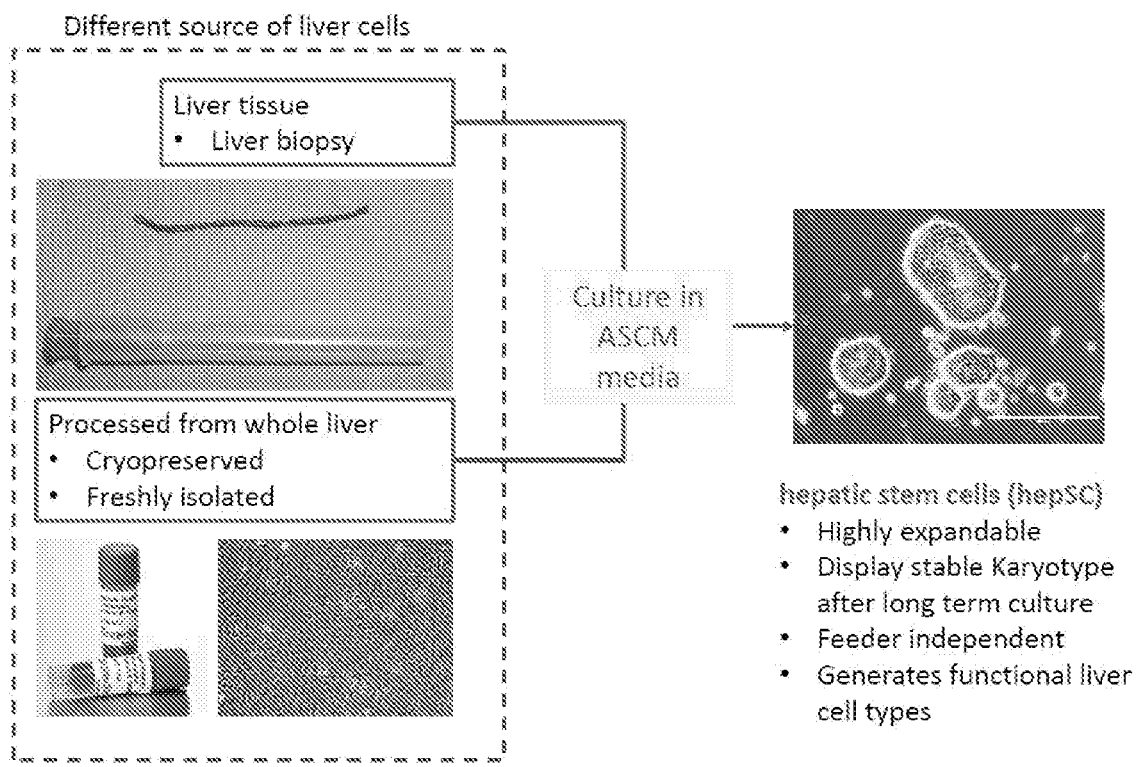
FIG. 2 shows a schematic representation of the derivation of adult stem cells from liver tissues (which include liver biopsy, cryopreserved or freshly isolated liver cells).

Provided herein is a cell culture medium for preparing a stem cell from a differentiated cell or maintaining a stem cell in the undifferentiated state.

In one aspect, there is provided a cell culture medium for preparing a stem cell from a differentiated cell or maintaining a stem cell in the undifferentiated state, the cell culture medium comprising:
  a) a base medium;
  b) an ABL and SRC dual kinase inhibitor, or an ABL kinase inhibitor and a SRC kinase inhibitor;
  c) a mitogenic factor; and
  d) a WNT signalling pathway activator.

The term "stem cell" can refer to either a pluripotent stem cell, or a committed precursor cell, both as defined above. Minimally, a stem cell has the ability to proliferate and form cells of more than one different phenotype, and is also capable of self renewal—either as part of the same culture, or when cultured under different conditions As used in this disclosure, "differentiated" and "undifferentiated" are relative terms depending on the context in which they are used. Specifically, in reference to a particular type of self-renewing stem cell, the term "undifferentiated" refers back to the same self-renewing stem cell, whereas the term "differentiated" refers to one or more of the relatively mature phenotypes the stem cell can generate—as discernable by morphological criteria, antigenic markers, and gene transcripts they produce.

As used herein, the term "cell culture medium" refers to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, cell culture production medium which is formulated to promote recombinant protein production or cell culture derivation medium which is formulated to derive various cell types (e.g. to derive a stem cell from a differentiated cell). The terms nutrient, ingredient, and component are used interchangeably herein to refer to the constituents that make up a cell culture medium.

In one embodiment, there is provided a cell culture medium for preparing a stem cell from a differentiated cell, the cell culture medium comprising:
  a) a base medium;
  b) an ABL kinase inhibitor and a SRC kinase inhibitor, or an ABL and SRC dual kinase inhibitor;
  c) a mitogenic factor; and
  d) a WNT signalling pathway activator.

In one embodiment, there is provided a cell culture medium for maintaining a stem cell in the undifferentiated state, the cell culture medium comprising:
  a) a base medium;
  b) an ABL kinase inhibitor and a SRC kinase inhibitor, or an ABL and SRC dual kinase inhibitor;
  c) a mitogenic factor; and
  d) a WNT signalling pathway activator.

In one embodiment, there is provided a cell culture medium for preparing a stem cell from a differentiated cell or maintaining a stem cell in the undifferentiated state, the cell culture medium comprising:
  a) a base medium;
  b) an ABL kinase inhibitor;
  c) a mitogenic factor; and
  d) a WNT signalling pathway activator.

The ABL kinase inhibitor may be an ABL and SRC dual kinase inhibitor (e.g. Dasatinib). The cell culture medium may further comprise a SRC kinase inhibitor.

In one embodiment, the invention provides for a new culture condition that allows the derivation of adult stem cells from multiple adult human and mouse organs including liver, pancreas and colon. The adult stem cells may be stably passaged in the media with the following features a) dual inhibition of SRC and ABL kinase and b) independent of FGF agonist, BMP antagonist, Notch agonist and TGFb inhibitor. In one embodiment, the cell culture medium supports the feeder independent culture of stem cells. In one embodiment, the cell culture medium supports a 2D culture system. In one embodiment, the cell culture medium is an animal-free composition.

In one embodiment, there is provided a cell culture medium for preparing a stem cell from a differentiated cell or maintaining a stem cell in the undifferentiated state. The cell culture medium may comprise a base medium. The cell culture medium may comprise an ABL kinase inhibitor and a SRC kinase inhibitor, or an ABL and SRC dual kinase inhibitor. The cell culture may comprise a mitogenic factor. The cell culture medium may further comprise a WNT signalling pathway activator.

In one embodiment, there is provided a cell culture medium. The cell culture medium may comprise an ABL kinase inhibitor and a SRC kinase inhibitor, or an ABL and SRC dual kinase inhibitor. The cell culture medium may comprise an ABL kinase inhibitor wherein the ABL kinase inhibitor is an ABL and SRC dual kinase inhibitor (such as Dasatinib).

In one embodiment, there is provided a cell culture medium. The cell culture medium may comprise a base medium. The cell culture medium may comprise an ABL kinase inhibitor and a SRC kinase inhibitor, or an ABL and SRC dual kinase inhibitor.

In one embodiment, there is provided a cell culture medium. The cell culture medium may comprise a base medium. The cell culture medium may comprise an ABL kinase inhibitor and a SRC kinase inhibitor, or an ABL and SRC dual kinase inhibitor. The cell culture may comprise a mitogenic factor.

In one embodiment, there is provided a cell culture medium. The cell culture medium may comprise a base medium. The cell culture medium may comprise an ABL kinase inhibitor and a SRC kinase inhibitor, or an ABL and SRC dual kinase inhibitor. The cell culture may comprise a mitogenic factor. The cell culture medium may further comprise a WNT signalling pathway activator.

The differentiated cell may be derived from the endoderm lineage. In one embodiment, the differentiated cell is a differentiated cell from the Gut lineage. In one embodiment, the differentiated cell is a differentiated cell from the Foregut lineage or Hindgut lineage. The differentiated cell may be a differentiated cell from the Posterior foregut lineage. The differentiated cell may be a differentiated cell from the liver, pancreas, colon, stomach or intestine.

In one embodiment, the differentiated cell is a liver, pancreatic, gastric, colon cell or intestinal cell. The intestinal cell may be a cell from the small intestine (i.e. duodenum, jejunum, and ileum). The intestinal cell may be a cell from the large intestine (i.e. cecum, colon, rectum and anal canal).

In one embodiment, the differentiated cell is a hepatic parenchymal cell. The hepatic parenchymal cell may be a hepatocytes or a cholangiocyte.

The differentiated cell may be a differentiated cell from a mammal. Suitable mammals that fall within the scope of the invention include, but are not restricted to, humans, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deers).

In one embodiment, the differentiated cell is from an isolated tissue or cell sample. The tissue sample may be a biopsy sample. The isolated cell sample may be cryopreserved sample.

In one embodiment, the stem cell is of a Gut lineage. In one embodiment, the stem cell is from the Foregut or Hindgut lineage. In one embodiment, the stem cell is from the Posterior Foregut lineage. In one embodiment, the stem cell is a liver, pancreatic, gastric, colon or intestinal stem cell.

The term "base medium" or "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. The base medium may comprise a component selected from the group consisting of advance DMEM, HEPEs, L-glutamine, N-2 supplement and B-27 supplement.

The ABL kinase inhibitor may be Dasatinib (BMS-354825), Imatinib (STI571), Nilotinib (AMN107), Bosutinib (SKI-606), PP121, GNF-5, GNF-7, Bafetinib (INNO-406), Radotinib, Nocodazole or Ponatinib (AP24534).

The SRC kinase inhibitor may be Dasatinib (BMS-354825), Bosutinib (SKI-606), Ponatinib (AP24534), KX2-391, Saracatinib, PP1, P2, Src Inhibitor-1, Quercetin, WH-4-023, MNS (3,4-Methylenedioxy-β-nitrostyrene, MDBN), SU6656, CCT196969, PP121, TPX-0005, NVP-BHG712 or KX2-391.

In one embodiment, the SRC kinase inhibitor is Src Inhibitor-1 (SLK-1 or 4-(4'-Phenoxyanilino)-6,7-dimethoxyquinazoline, 6,7-Dimethoxy-N-(4-phenoxyphenyl)-4-quinazolinamine).

In one embodiment, the ABL kinase inhibitor is a SRC kinase inhibitor.

In one embodiment, the ABL kinase inhibitor and the SRC kinase inhibitor is selected from the group consisting of Dasatinib (BMS-354825), Bosutinib (SKI-606), Ponatinib (AP24534) and PP121. In one embodiment, the ABL kinase inhibitor and the SRC kinase inhibitor is Dasatinib (BMS-354825).

In one embodiment, the ABL and SRC dual kinase inhibitor is selected from the group consisting of Dasatinib (BMS-354825), Bosutinib (SKI-606), Ponatinib (AP24534) and PP121. In one embodiment, the ABL and SRC dual kinase inhibitor is Dasatinib (BMS-354825).

The term "mitogeneic factor" may refer to a chemical or biological substance, such as a protein molecule, which induces a cell to begin cell division. The mitogenic factor may be EGF, VEGF, NGF, PDGF, HGF, IGF orTGF/Activin. In one embodiment, the mitogenic factor is an EGFR activator. In one embodiment, the mitogenic factor is EGF.

In one embodiment, the WNT signalling activator activates the beta-catenin pathway. The WNT signalling activator can be a Wnt agonist. The Wnt agonist may be a Wnt family member (Wnt-1/Int-1, Wnt-2/Irp (Int-1-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, and Wnt-16); an R-spondin family member (R-spondin 1, R-spondin 2, R-spondin 3, and R-spondin 4); Norrin (Norrie Disease Protein or NDP) or a Glycogen synthase kinase 3 inhibitor.

In one embodiment, the WNT signalling activator is a Wnt ligand, an R-Spondin ligand or a Glycogen synthase kinase 3 inhibitor.

In one embodiment, the WNT signalling activator is R-Spondin 1.

The Glycogen synthase kinase 3 inhibitor may be a Glycogen synthase kinase 3a inhibitor or Glycogen synthase kinase 3b inhibitor.

In one embodiment, the GSK3 inhibitor is selected from the group consisting of CHIR-98014, CHIR-99021, SB216763, TWS119, Tideglusib, SB415286, BIO, AZD2858, AZD1080, AR-A014418, TDZD-8, LY2090314, Bikinin, 1-Azakenpaullone, BIO-acetoxime and IM-12.

In one embodiment, the GSK3 inhibitor is selected from the group consisting of CHIR-98014 and CHIR-99021. In one embodiment, the GSK3 inhibitor is CHIR-98014. In one embodiment, the GSK3 inhibitor is CHIR-99021.

In one embodiment, the WNT signalling activator is R-Spondin 1 and a GSK3 inhibitor. In one embodiment, the WNT signalling activator is R-Spondin 1 and a GSK3 inhibitor selected from CHIR-98014 and CHIR-99021.

In one embodiment, the cell culture medium further comprises a stimulator for NAD+ and NADP+ generation.

In one embodiment, the stimulator for NAD+ and NADP+ generation is nicotinamide. The stimulator for NAD+ and NADP+ generation may be a chemical derivative of nicotinamide.

In one embodiment, the cell culture medium further comprises a cAMP/PKA pathway activator. In one embodiment, the cAMP/PKA pathway activator is an endotoxin. In one embodiment, the cAMP/PKA pathway activator is cholera toxin or a fragment thereof. In one embodiment, the cAMP/PKA pathway activator is cholera toxin.

In one embodiment, there is provided a cell culture medium for preparing a stem cell from a differentiated cell or maintaining a stem cell in the undifferentiated state, the cell culture medium comprising:
- a) a base medium;
- b) Dasatinib;
- c) EGF; and
- d) R-Spondin 1.

In one embodiment, there is provided a cell culture medium for preparing a stem cell from a differentiated cell or maintaining a stem cell in the undifferentiated state, the cell culture medium comprising:
- a) a base medium;
- b) Dasatinib;
- c) EGF;
- d) R-Spondin 1; and
- e) CHIR-98014.

In one embodiment, there is provided a cell culture medium for preparing a stem cell from a differentiated cell or maintaining a stem cell in the undifferentiated state, the cell culture medium comprising:
- a) a base medium;
- b) Dasatinib;
- c) EGF;
- d) R-Spondin 1; and
- e) nicotinamide.

In one embodiment, there is provided a cell culture medium for preparing a stem cell from a differentiated cell or maintaining a stem cell in the undifferentiated state, the cell culture medium comprising:
- a) a base medium;
- b) Dasatinib;
- c) EGF;
- d) R-Spondin 1; and
- e) cholera toxin.

In one embodiment, there is provided a cell culture medium for preparing a stem cell from a differentiated cell or maintaining a stem cell in the undifferentiated state, the cell culture medium comprising:
- a) a base medium;
- b) Dasatinib;
- c) EGF;
- d) R-Spondin 1; and
- e) nicotinamide; and
- f) cholera toxin.

In one embodiment, the cell culture medium does not comprise a component selected from the group consisting of:
- a) an FGF agonist;
- b) a BMP antagonist;
- c) Notch agonist; and
- d) a TGFβ inhibitor.

In one aspect, there is provided a cell culture medium for preparing a stem cell from a differentiated cell or maintaining a stem cell in the undifferentiated state, the cell culture medium comprising:
- a) a base medium;
- b) an ABL kinase inhibitor and a SRC kinase inhibitor;
- c) a mitogenic factor; and
- d) a WNT signalling pathway activator.

In one aspect, there is provided a cell culture medium for preparing a stem cell from a differentiated cell or maintaining a stem cell in the undifferentiated state, the cell culture medium comprising:
- a) a base medium;
- b) an ABL and SRC dual kinase inhibitor;
- c) a mitogenic factor; and
- d) a WNT signalling pathway activator.

In one aspect, there is provided a method for preparing a stem cell from a differentiated cell, the method comprising contacting a differentiated cell with a cell culture medium as defined herein for a time and under conditions to derive a stem cell from the differentiated cell.

In one aspect, there is provided a method for maintaining a stem cell in the undifferentiated state, the method comprising the step of culturing a stem cell with a cell culture medium as defined herein for a time and under conditions sufficient to maintain the stem cell in the undifferentiated state.

In one embodiment, the method further comprises culturing the stem cell in a feeder-free 2 dimensional culture.

In one aspect, there is provided a stem cell obtained according to a method as defined herein.

In one embodiment, the stem cell expresses a marker selected from the group consisting of SOX9, KI67 and HNF4A.

In one embodiment, the stem cell expresses a marker selected from the group consisting of SOX9 and KI67.

In one embodiment, the stem cell is a hepSC and expresses HNF4A, SOX9 and KI67.

In one embodiment, the stem cell is a pancreatic stem cell or a colon stem cell and expresses SOX9 and KI67 but has low levels of HNF4A.

In one embodiment, there is provided a stem cell obtained according to a method as defined herein for use in therapy.

In one embodiment, there is provided the use of a cell culture medium as defined herein for preparing a stem cell from a differentiated cell or maintaining a stem cell in the undifferentiated state.

In one embodiment, there is provided the use of a stem cell as defined herein in the manufacture of a medicament for the treatment of a disease. The disease may, for example, be a liver failure or dysfunction or diabetes (such as Type I diabetes).

The terms "treat", "treating" or "treatment" of any disease or disorder refers to ameliorating the disease or disorder (e.g. slowing or arresting or reducing the development of the disease or at least one of the clinical symptoms thereof), to preventing or delaying the onset or development or progression of the disease or disorder.

In one embodiment, there is provided a kit comprising a cell culture medium as described herein. In one embodiment, there is provided a kit comprising a stem cell obtained according to a method as defined herein. In one embodiment, the kit further comprises reagents for isolating cells from a tissue, such as a collagenase digestion solution.

As used in this application, the singular form "a," "an," and "the" include plural references unless the context clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Figure 3:
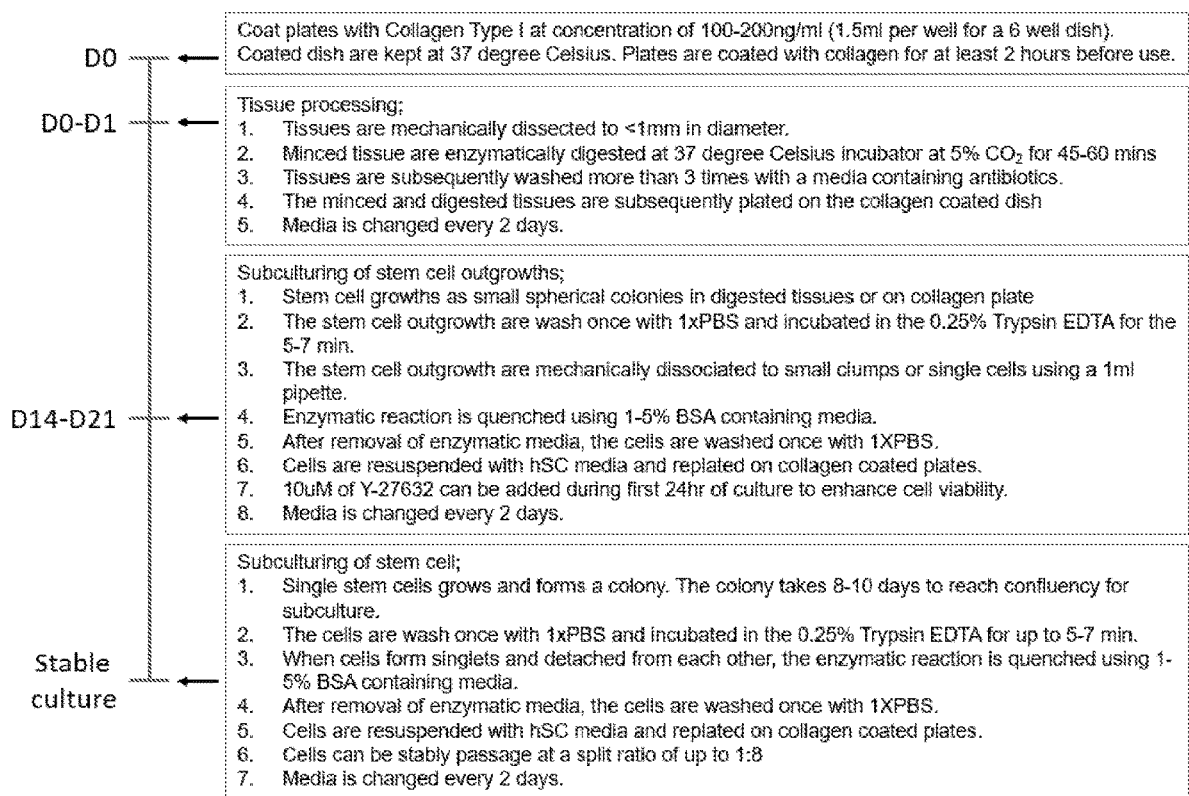
FIG. 3 shows the overview of the protocol for the derivation of stem cells from adult liver tissue biopsy (human and mouse).
Figure 4:
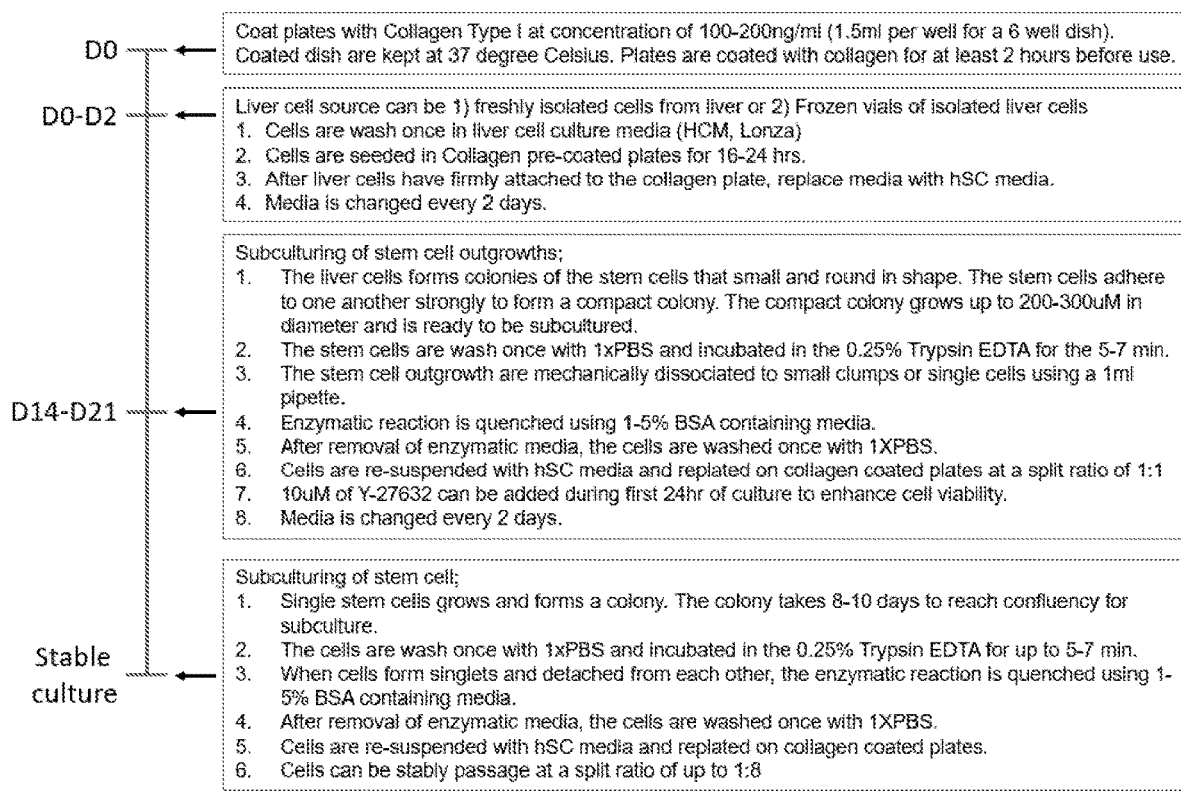
FIG. 4 shows the overview of the protocol for the derivation of stem cells from isolated liver cells.

Materials and Methods
Derivation of Stem Cells from Adult Liver Tissue Biopsy (Human and Mouse) (FIG. 3)
Coating of Plates
Plates are coated with Collagen Type I at concentration of 100-200 ng/ml (1.5 ml per well for a 6 well dish). Coated dish are kept at 37 degree Celsius. Plates are coated with collagen for at least 2 hours before use
Tissue Processing
1. Tissues are mechanically dissected to <1 mm in diameter.
2. Minced tissue are enzymatically digested at 37 degree Celsius incubator at 5% $CO_2$ for 45-60 mins
3. Tissues are subsequently washed more than 3 times with a media containing antibiotics.
4. The minced and digested tissues are subsequently plated on the collagen coated dish
5. Media is changed every 2 days.
Subculturing of Stem Cell Outgrowths
1. Stem cell growths as small spherical colonies in digested tissues or on collagen plate
2. The stem cell outgrowth are wash once with 1×PBS and incubated in the 0.25% Trypsin EDTA for the 5-7 min.
3. The stem cell outgrowths are mechanically dissociated to small clumps or single cells using a 1 ml pipette.
4. Enzymatic reaction is quenched using 1-5% BSA containing media.
5. After removal of enzymatic media, the cells are washed once with 1×PBS.
6. Cells are resuspended with hSC media and replated on collagen coated plates.
7. 10 µM of Y-27632 can be added during first 24 hr of culture to enhance cell viability.
8. Media is changed every 2 days.
Subculturing of Stem Cell
1. Single stem cells grow and form a colony. The colony takes 8-10 days to reach confluency for subculture.
2. The cells are wash once with 1×PBS and incubated in the 0.25% Trypsin EDTA for up to 5-7 min.
3. When cells form singlets and detached from each other, the enzymatic reaction is quenched using 1-5% BSA containing media.
4. After removal of enzymatic media, the cells are washed once with 1×PBS.
5. Cells are resuspended with hSC media and replated on collagen coated plates.
6. Cells can be stably passage at a split ratio of up to 1:8
7. Media is changed every 2 days.
Derivation of Stem Cells from Isolated Liver Cells (FIG. 4)
Coating of Plates
Plates are coated with Collagen Type I at concentration of 100-200 ng/ml (1.5 ml per well for a 6 well dish). Coated dish are kept at 37 degree Celsius. Plates are coated with collagen for at least 2 hours before use Liver Cell Source
Liver cell source can be 1) freshly isolated cells from liver or 2) Frozen vials of isolated liver cells
1. Cells are wash once in liver cell culture media (HCM, Lonza)
2. Cells are seeded in Collagen pre-coated plates for 16-24 hrs.
3. After liver cells have firmly attached to the collagen plate, replace media with hSC media.
4. Media is changed every 2 days.
Subculturing of stem cell outgrowths;
1. The liver cells forms colonies of the stem cells that small and round in shape. The stem cells adhere to one another strongly to form a compact colony. The compact colony grows up to 200-300 uM in diameter and is ready to be subcultured.
2. The stem cells are wash once with 1×PBS and incubated in the 0.25% Trypsin EDTA for the 5-7 min.
3. The stem cell outgrowths are mechanically dissociated to small clumps or single cells using a 1 ml pipette.
4. Enzymatic reaction is quenched using 1-5% BSA containing media.
5. After removal of enzymatic media, the cells are washed once with 1×PBS.
6. Cells are re-suspended with hSC media and replated on collagen coated plates at a split ratio of 1:1
7. 10 µM of Y-27632 can be added during first 24 hr of culture to enhance cell viability.
8. Media is changed every 2 days.
Subculturing of Stem Cell
1. Single stem cells grow and form a colony. The colony takes 8-10 days to reach confluency for subculture.
2. The cells are wash once with 1×PBS and incubated in the 0.25% Trypsin EDTA for up to 5-7 min.
3. When cells form singlets and detached from each other, the enzymatic reaction is quenched using 1-5% BSA containing media.
4. After removal of enzymatic media, the cells are washed once with 1×PBS.
5. Cells are re-suspended with hSC media and replated on collagen coated plates.
6. Cells can be stably passage at a split ratio of up to 1:8

Example 1

Figure 5:
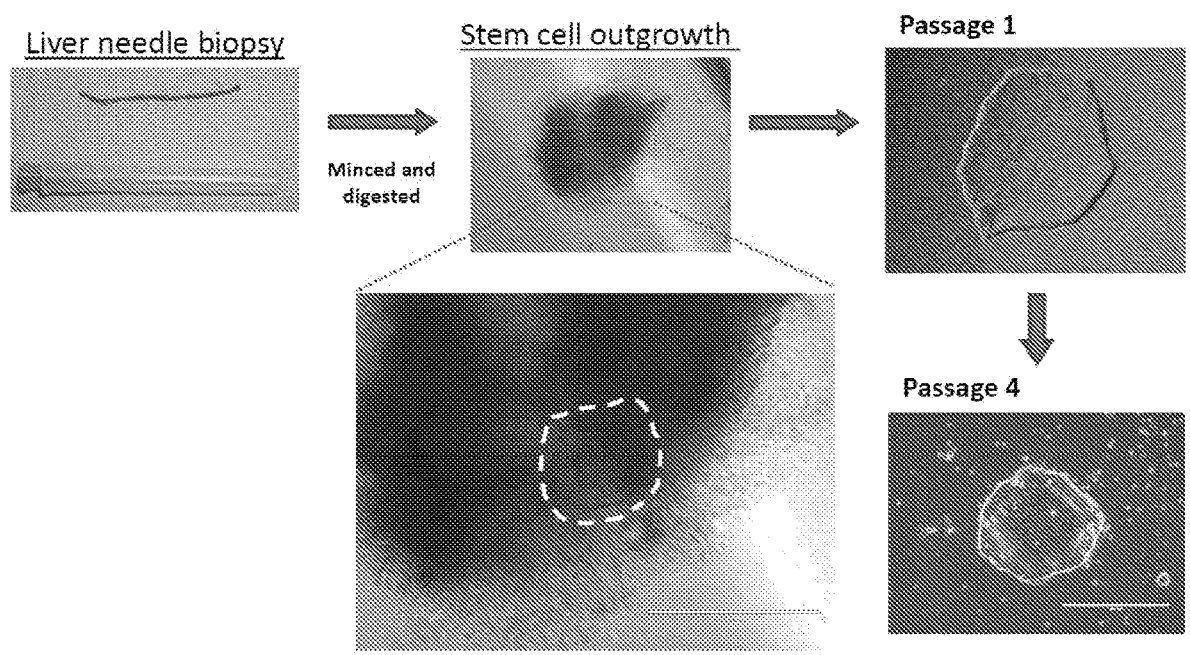
FIG. 5 shows the derivation of hepatocyte stem cell (hepSC) from human adult liver tissue.

ASC from Adult Liver Tissue
Derivation of hepSC from Human Adult Liver Tissue or Mouse Liver Tissue
The workflow of hepSC derivation from human adult liver tissue from a needle biopsy is shown in FIG. 5. Tissue that is mechanically dissected and enzymatically digested is plated on collagen plates. Small pieces of tissues attached to the collagen coated cell culture dishes and stem cell outgrowth can be detected (dotted circle) after 2-3 weeks of culture. The stem cell outgrowth is subcultured and single cells from the stem cell outgrowths form single colonies of hepSC in the first passage. These colonies can be stably cultured to generate more colonies of hepSCs.

Figure 7:
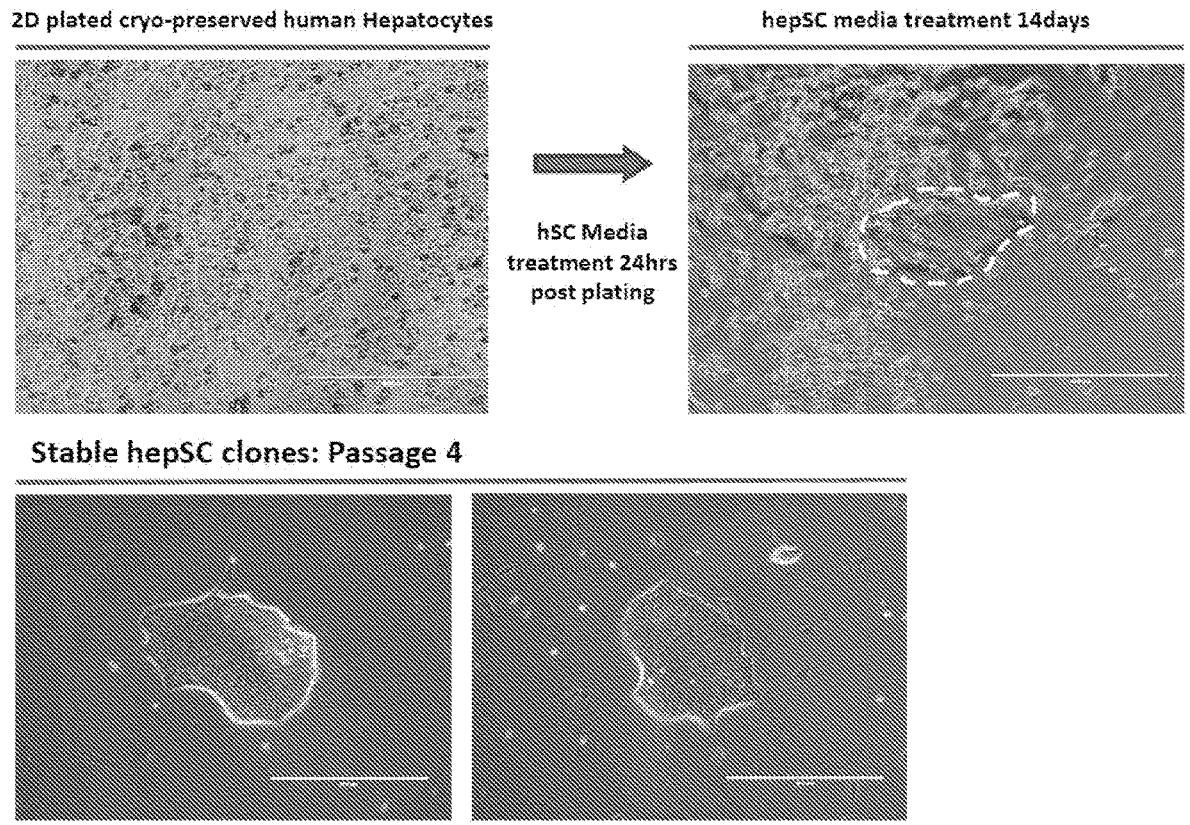
FIG. 7 shows the derivation of hepSC from cyro-preserved hepatocytes.

The same methodology can be used to derive hepSC from mouse liver tissue as shown in FIG. 6. FIG. 6(A) shows hepSC isolated from a NOD-SCID mouse liver while FIG. 6(B) shows hepSC isolated from mice of a different genetic background (C57BL/6).
Derivation of HepSC from Cyro-Preserved Hepatocytes
Cyro-preserved hepatocytes forms a monolayer with define boundaries between each cell after plating on collagen coated dish (FIG. 7). After 2 weeks of treatment, colonies of hepSC formed within the hepatocyte cultures. Some of the hepatocytes dies off after 2 weeks of prolong culture hepSC media and colonies of hepSC can be observed in the culture. These colonies of stem cells can be stably cultured and sustained as hepSC stem cells (Passage 4 hepSC colonies that have been culture for more than a month).

Expression of Stem Cell Markers in HepSC

The expression of stem cell markers SOX9 and HNF4A in hepSC are shown in FIG. 8.

Dasatinib Withdrawal from HSC Media

Figure 9:
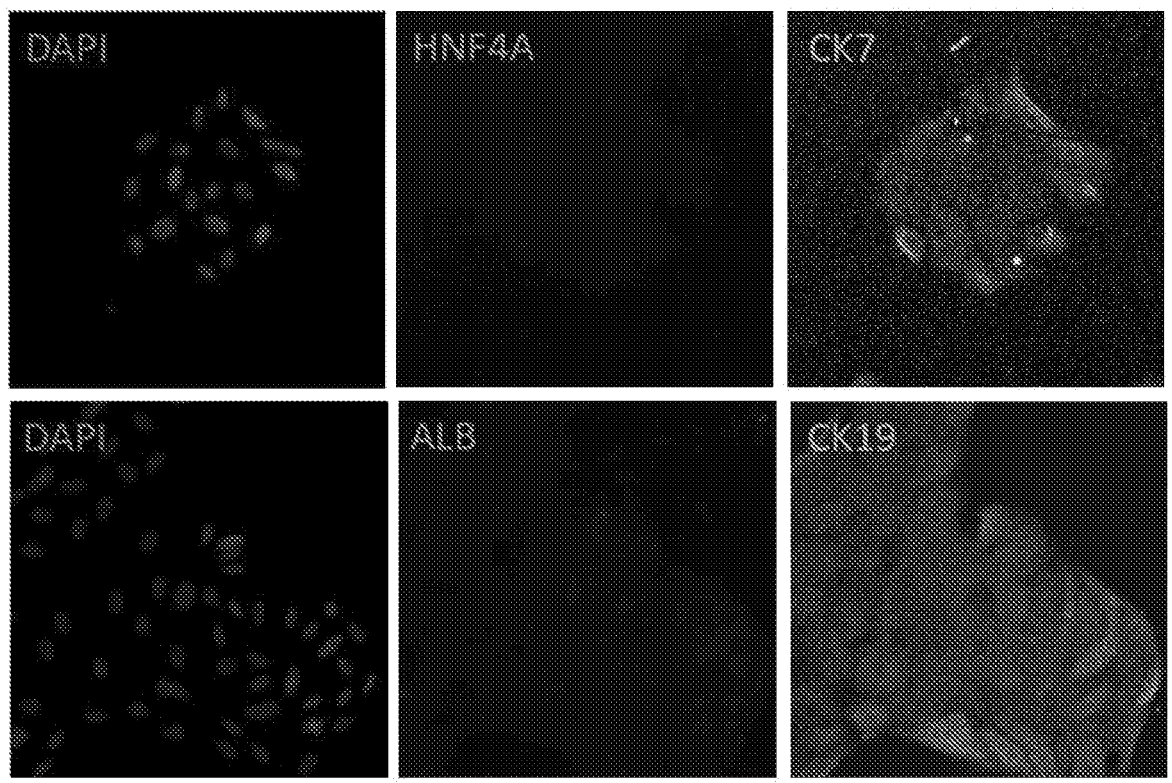
FIG. 9 shows that Dasatinib withdrawal from hSC media results in the loss of stem cell state in hepSC.

FIG. 9 shows that Dasatinib withdrawal from hSC media results in the loss of stem cell state in hepSC. Upon removal of Dasatinib from the media, the cells lose expression of stem cell marker HNF4A and start to express cholangiocyte markers CK7, CK19 and SOX9. There is also a loss of stem cell self renewing capacity and cells cannot be stably passaged.

Replacement of Dasatinib with Other ABL Kinase Inhibitor

FIG. 10 shows the replacement of Dasatinib with other ABL kinase inhibitor. Dasatinib was discovered as an inhibitor of Bcr-Abl tyrosine kinase inhibitor of chronic myelogenous leukemia. Subsequent studies suggest that Dasatinib inhibits SRC, c-KIT, PDGF and EPHA as well. Imatinib is another BCR-ABL tyrosine kinase inhibitor design based on Pyrimidine A which is identified in a high-throughput screen. Nilotinib is a phenylamino-pyrimidine derivative that is structurally related to Imatinib.

Figure 11:
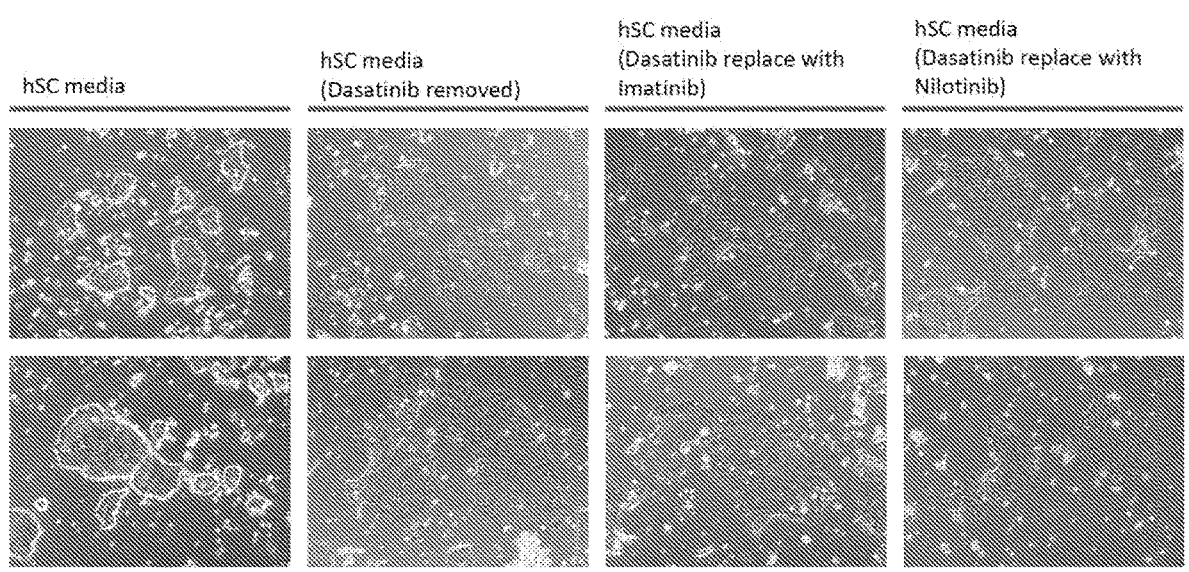
FIG. 11 shows that Dasatinib cannot be replaced by other ABL kinase inhibitors Imatinib and Nilotinib.

Dasatinib cannot be replaced by other ABL kinase inhibitors Imatinib and Nilotinib (FIG. 11). Within 48 hrs, removal of Dasatinib results in drastic cell morphology changes. Cells loses small compact epithelial morphology, becomes large fibroblastic and colonies are less compact. Replacement of Dasatinib with Imatinib or Nilotinib did not rescue cell morphology changes.

Figure 12:
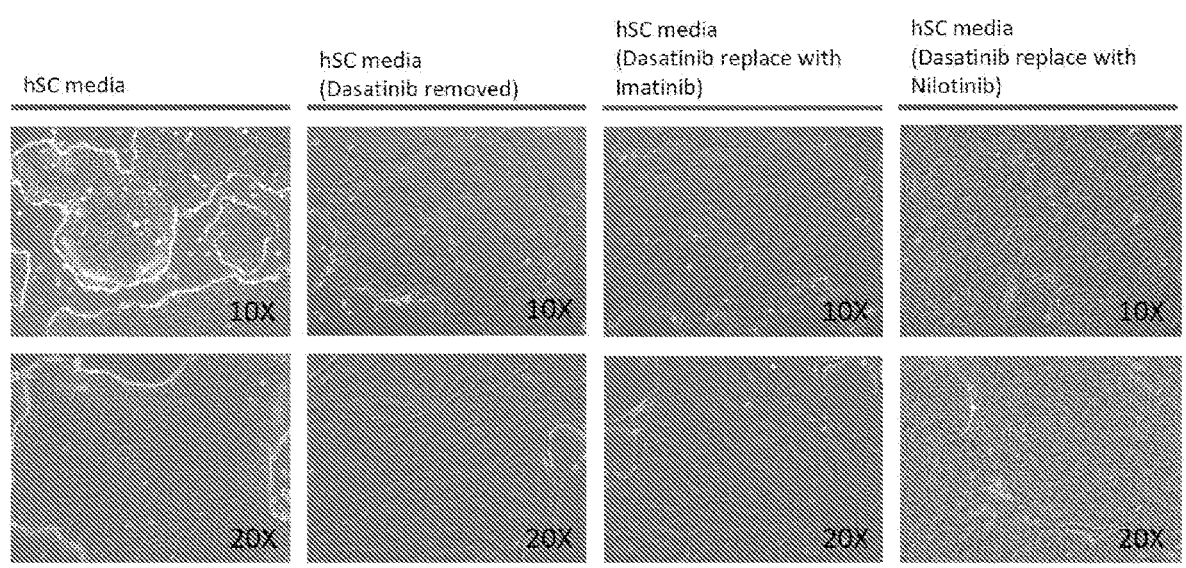
FIG. 12 shows that cells without Dasatinib completely differentiated 6 days after withdrawal. Addition of Imatinib or Nilotinib did not rescue the cell phenotype.
Figure 13:
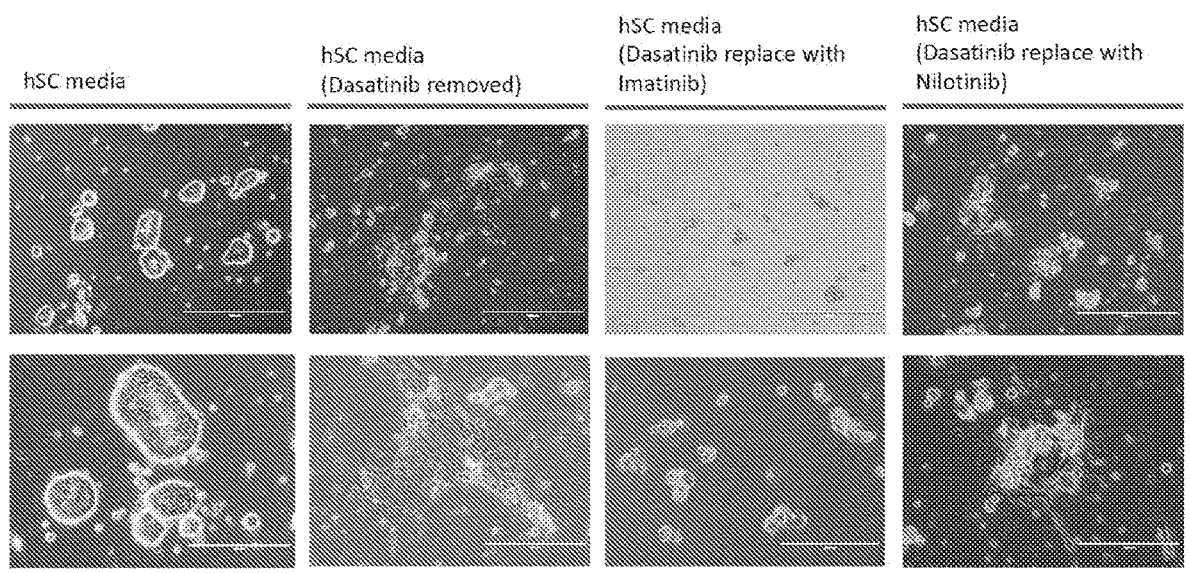
FIG. 13 shows the image of cells 48 hr after subculturing without Dasatinib. Addition of Imatinib or Nilotinib did not rescue the cell phenotype.

FIG. 12 shows that cells without Dasatinib completely differentiated 6 days after withdrawal. Addition of Imatinib or Nilotinib did not rescue the cell phenotype. FIG. 13 shows the image of cells 48 hr after subculturing. Cells without Dasatinib poorly survive the passage even in the presence of Rock inhibitors. Addition of Imatinib or Nilotinib did not rescue the phenotype. Cells float in very small clumps. A few cells manage to attach. Looks like fibroblast and do not proliferate. Bubbles observed in these cells, suggesting cells are dying.

Replacement of Dasatinib with SRC inhibitor or ABL kinase inhibitor+SRC inhibitor is shown in the table of FIG. 10. Inhibition of BCR-ABL, c-KIT and PDGF alone is insufficient to replace Dasatinib. Dasatinib may be functioning through SRC or EPHA as well.

Figure 14:
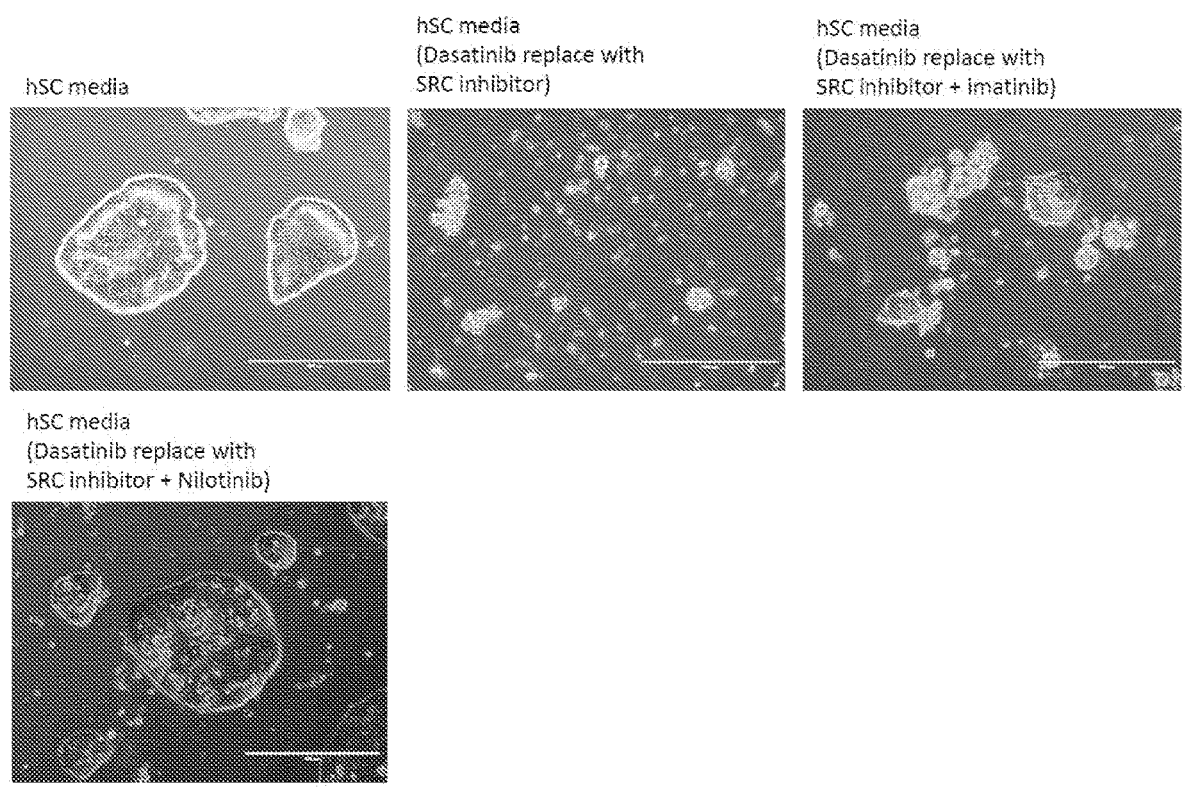
FIG. 14 shows the replacement of Dasatinib with SRC inhibitor or ABL kinase inhibitor+SRC inhibitor.

FIG. 14 shows the replacement of Dasatinib with SRC inhibitor or ABL kinase inhibitor+SRC inhibitor. SRC inhibition alone cannot replace function of the Dasatinib. SRC inhibition together with Imatinib or Nilotinib seems to improved survival of hepatic stem cells with Dasatinib. Dasatinib function in hSC media can potentially be replaced by 2 chemicals to target both ABL kinases and SRC kinases Example 2

ASC from Adult Pancreatic Tissue

Figure 16:
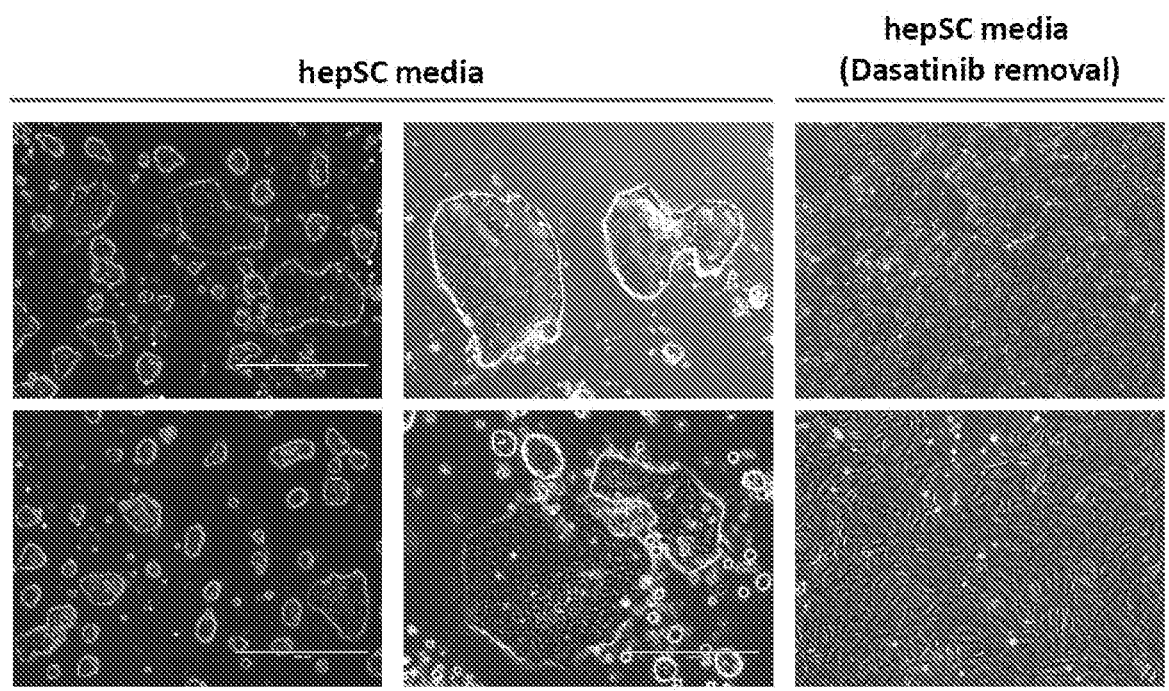
FIG. 16 shows the derivation of human pancreatic stem cell (PanSC) with hepSC media and loss of colony morphology after removal of Dasatinib.

A similar strategy and protocol can be applied to adult pancreatic tissue to isolate pancreatic stem cells (PanSC) (FIG. 15). FIG. 16 shows the derivation of human pancreatic stem cell (PanSC) with hepSC media. FIG. 16 shows the stable culture of pancreatic stem cells in the hepSC media. Withdrawal of Dasatinib results in rapid loss of stem cell morphology. Cells appear fibroblastic and spread across the dish instead of forming distinct tight colonies.

Figure 17:
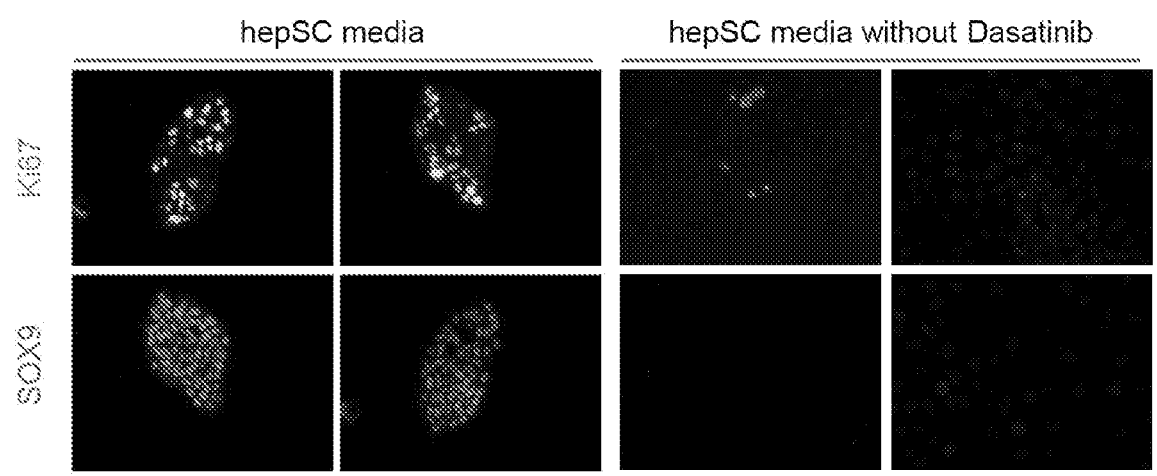
FIG. 17 shows that PanSC losses stem cell properties after Dasatinib removal.

PanSC losses stem cell properties after Dasatinib removal (FIG. 17). There is a drastic decrease in the expression of stem cell marker SOX9 and proliferation marker KI67 in the cells after Dasatinib removal. The cells no longer proliferate and maintain the stem cell state.

Example 3

ASC from Adult Colon Tissue

A similar strategy and protocol can be applied to adult colon tissue to isolate colon stem cells (CoSC) (FIG. 18). Adult colon stem cells can be stably cultured (FIG. 19). Cells have been stably propagated for more than 80 days. The colon stem cells forms a much compacted colony compared to the pancreatic and liver stem cells.

The invention claimed is:

1. A method for preparing a stem cell from a differentiated cell from the gut lineage, the method comprising contacting a differentiated cell from the gut lineage with a cell culture medium comprising: a) a base medium; b) an ABL and SRC dual kinase inhibitor, or an ABL kinase inhibitor and a SRC kinase inhibitor; c) a mitogenic factor; and d) a WNT signalling pathway activator, for a time and under conditions to derive a stem cell from the differentiated cell.

2. The method of claim 1, wherein the differentiated cell is a differentiated cell from the Foregut or Hindgut lineage.

3. The method of claim 2, wherein the Foregut lineage differentiated cell is a Posterior Foregut differentiated cell.

4. The method of claim 1, wherein the base medium comprises a component selected from the group consisting of advance DMEM, HEPEs, L-glutamine, and N-2 supplement.

5. The method of claim 1, wherein the ABL kinase inhibitor is selected from the group consisting of Dasatinib (BMS-354825), Imatinib (STI571), Nilotinib (AMN107), Bosutinib (SKI-606), PP121, GNF-5, GNF-7, Bafetinib (INNO-406), Radotinib, Nocodazole and Ponatinib (AP24534) and wherein the SRC kinase inhibitor is selected from the group consisting of Dasatinib (BMS-354825), Bosutinib (SKI-606), Ponatinib (AP24534), KX2-391, Saracatinib, PP1, PP2, Src Inhibitor-1, Quercetin, WH-4-023, MNS, SU6656, CCT196969, PP121, TPX-0005, NVP-BHG712 and KX2-391.

6. The method of claim 1, wherein the ABL and SRC dual kinase inhibitor is selected from the group consisting of Dasatinib (BMS-354825), Bosutinib (SKI-606), Ponatinib (AP24534) and PP121.

7. The method of claim 1, wherein the mitogenic factor is selected from the group consisting of EGF, VEGF, NGF, PDGF, HGF, IGF, TGF, and Activin.

8. The method of claim 1, wherein the WNT signalling pathway activator is a Wnt ligand, an R-Spondin ligand or a Glycogen synthase kinase 3 (GSK3) inhibitor, optionally wherein the WNT signalling pathway activator is R-Spondin 1 or a GSK3 inhibitor.

* * * * *